(12) United States Patent
Silva et al.

(10) Patent No.: US 7,346,411 B2
(45) Date of Patent: Mar. 18, 2008

(54) AUTOMATIC CONTROL AND MONITORING SYSTEM FOR SPLICE OVERLAPPING TOLERANCE IN TEXTILE PLY

(75) Inventors: Nuno Filipe Martins Silva, Abade Neiva (PT); Andre Teixeira Puga, Vila Nova de Gaia (PT); Antonio Alberto da Silva Maia, S. Mamede Da Infesta (PT); Ireneu Manuel Silva Dias, Senhora da Hora (PT); Agostinho Jose Barbosa Ferreira, Senhora da Hora (PT); Filipe de Sousa Pinto, S. Mamede de Infesta (PT)

(73) Assignee: Continental Mabor-Industria de Pneus, S.A., Lousado (PT)

( * ) Notice: Subject to any disclaimer, the term of this patent is extended or adjusted under 35 U.S.C. 154(b) by 261 days.

(21) Appl. No.: 10/527,003

(22) PCT Filed: Aug. 29, 2003

(86) PCT No.: PCT/PT03/00012

§ 371 (c)(1),
(2), (4) Date: Jul. 27, 2005

(87) PCT Pub. No.: WO2004/022323

PCT Pub. Date: Mar. 18, 2004

(65) Prior Publication Data

US 2006/0041327 A1    Feb. 23, 2006

(30) Foreign Application Priority Data

Sep. 3, 2002    (PT) ..................................... 102835

(51) Int. Cl.
*G01N 21/892*    (2006.01)

(52) U.S. Cl. ...................... 700/110; 700/143; 382/152; 356/430; 250/358.1; 156/64; 156/350; 156/351; 156/366; 156/378.1; 702/82; 702/84; 348/88; 348/92; 348/93

(58) Field of Classification Search .. 250/358.1–360.1, 250/559.05, 84, 559.08, 559.07; 156/559.07, 156/64, 350–351, 360, 367, 378; 73/378, 73/146, 159, 866, 865.8; 702/865.8, 82, 702/FOR. 137, 84; 348/88, 92, 93; 356/430–431; 28/93, 141, 299; 700/110, 302, 143, 204
See application file for complete search history.

(56) References Cited

U.S. PATENT DOCUMENTS 3,773,422 A    11/1973 Stavis et al.
(Continued)

FOREIGN PATENT DOCUMENTS

EP    329889 A2 *    8/1989
(Continued)

OTHER PUBLICATIONS

Patent Abstracts of Japan; vol. 008, No. 143, Jul. 4, 1984 & JP 59 039538 A (Yokohama Gomu KK), Mar. 3, 1984.
(Continued)

*Primary Examiner*—Thomas P. Noland
(74) *Attorney, Agent, or Firm*—Darby & Darby P.C.

(57) ABSTRACT

The present system enables the monitoring and automatic control of the tolerance in splice overlap of textile play , though the identification of the overlap area, identification and counting of textile cords in the overlap area, and the generation of a control signal for the manufacturing equipment based on parameters and criteria defined by a user. The system includes an image acquisition sub-assembly that contains a lighting module, artificial vision module, and respective elements of support, fixation, conditioning and adjustment. The system also includes a quality control computer program that has a module of morphologic image analysis for detection and recognition of the overlap of the ply, detecting and counting of cords in the overlap area, a module of support to the decision of acceptance/rejection of the ply based on parameters defined by the user and a module of an interface with production equipment.

26 Claims, 3 Drawing Sheets

U.S. PATENT DOCUMENTS

| | | | |
|---|---|---|---|
| 3,997,783 A * | 12/1976 | Boutaine et al. | 250/303 |
| 4,277,178 A * | 7/1981 | Cushing et al. | 356/431 |
| 4,842,413 A * | 6/1989 | Kuijpers et al. | 356/430 X |
| 4,892,609 A * | 1/1990 | Nakanome et al. | 156/406.4 |
| 5,256,883 A * | 10/1993 | Weichmann et al. | 356/430 X |
| 5,294,973 A | 3/1994 | Byrne | |
| 5,895,845 A * | 4/1999 | Burger | 73/146 |
| 7,083,082 B2 * | 8/2006 | Byskov et al. | 235/375 |

FOREIGN PATENT DOCUMENTS

| | | | | |
|---|---|---|---|---|
| EP | 366235 A1 * | 5/1990 | | 348/E3.018 |
| EP | 392693 A * | 10/1990 | | |
| EP | 0 692 714 A1 | 1/1996 | | |
| EP | 757245 A2 * | 2/1997 | | |
| EP | 869330 A2 * | 10/1998 | | |
| NL | 9500151 A * | 9/1996 | | |
| WO | WO-92/03721 A1 | 3/1992 | | |

OTHER PUBLICATIONS

Patent Abstracts of Japan; vol. 015, No. 107, Mar. 14, 1991 & JP 03 002511 A (Bridgestone Corp), Jan. 8, 1991.

Patent Abstracts of Japan; vol. 013, No. 104, Mar. 13, 1989 & JP 63 285453 A (Bridgestone Corp), Nov. 22, 1988.

* cited by examiner

AUTOMATIC CONTROL AND MONITORING SYSTEM FOR SPLICE OVERLAPPING TOLERANCE IN TEXTILE PLY

Cross reference to Prior Application

This is a U.S. national phase application under 35 U.S.C. §371 of International Pat. Application No. PCT/PT2003/000012, filed Aug. 29, 2003, and claims benefit of Portugese Patent Application No. 102835, filed Sep. 3, 2002 which is incorporated by reference herein. The International Application was published in English on Mar. 18, 2004 as WO 2004/022323 A1 under PCT Article 21(2).

INVENTION FIELD

The present invention is included in the area of industrial control of the tyre manufacturing process.

PREVIOUS INVESTIGATION

The manufacture of tyres is the object of a very rigorous and demanding quality control that targets the guarantee of safety conditions since the physical integrity of people depends on their utilisation.

Under the present manufacturing conditions no tyre with any type of defect reaches the market since quality control is exhaustive, all tyres are tested, instead of statistical, by sample. This fact bears significant costs, since defects are not always detected at the initial manufacturing stages causing a significant waste of finished product.

One of the aspects that are identified as the originator of defects is the splice of the textile ply. A wrongly done splice consists of an overlap with a reduced or excessive number of cords or textile thread. A system that does the counting of this number of threads will enable the elimination of a significant number of defects and contribute towards a pronounced reduction of costs.

The present invention views the solving of this problem through an automatic control and monitoring system of the tolerance of splice overlap in textile ply, which enables the identification of the overlap area and counting of thread or cord fabric, and the generation of a control signal for the remaining manufacturing equipment.

State of the Technique

The continuous monitoring of textile ply splices used in the tyre manufacturing is not referred to in any patent of the knowledge of inventors. The research carried out allowed some patents in the tyre manufacturing area to be identified, which are not concerned with the manufacturing stage within which the present invention is encompassed: EP 0 869 330 A2, Apparatus for testing tyre tread depth, where it is intended to determine the depth of the tyre's tread; U.S. Pat. No. 4,892,609, Automatic material feeder in tire forming machine, which is encompassed by manufacturing and not by quality control; U.S. Pat. No. 5,895,845, Method and gauge for measuring the tread depth of a motor vehicle tire, of a similar scope to EP 0 869 330 A2; U.S. Pat. No. 3,997,783, Method for testing the adhesion between the rubber compound and the cord fabric of a pneumatic tyre, which refers to the quality control of the adhesion between thread or cord fabric and the rubber. Since this deals with the analysis of the characteristics of a continuous ply, research was carried out and some patents were found in this area, but they do not contemplate the relevant aspects of this invention. Therefore, the patents EP 0 366 235 A1, Monitoring systems and methods; EP 0 392 693 A2, Online texture sensing; U.S. Pat. No. 5,256,883, Method and system for broad area field inspection of a moving web, particularly a printed web; EP 0 757 245, Apparatus for detecting streaky surface defects; NL 9 500 151, Method and apparatus for inspecting a web of material for defects, using the method in preparing a magazine reel in a reel changer, and reel changer provided with such an apparatus; U.S. Pat. No. 4,277,178, Web element concentration detection system, refer to the analysis of the surface of plies, detection of elements, failures, textures, and not to the analysis in its thickness as is the case of the present invention. The patent EP 0 329 889 A2, Method and apparatus for analysing a web of material, generates the profile of thickness of a ply or similar, but differs from the present invention because the present one detects and counts elements, thread or cord fabric, instead of simply detecting the occurrence of a different thickness. The patent U.S. Pat. No. 4,842,413, Apparatus for assessing the weld in belt layers for radial pneumatic tires, analysis the alignment conditions of the surface of the metallic plies for radial pneumatic tyres but once again the analysis does not refer to the thickness of the ply nor to the counting of the elements but to the alignment of layers.

In terms of commercial products, the inventors are unaware of the existence of any product that solves the problem the present invention intends to solve. Bytewise, an American company, commercialises a product that enables the monitoring and measurement of the thickness of the overlap splice of textile ply in tyre manufacturing. Nevertheless, it does not count the threads and the information it supplies, thickness of the overlap has little interest, once the quality of the product depends on the existence of an adequate number of cord fabric and not simply of the thickness of the splice. The contrary may occur, where the thickness is adequate but the overlap does not contain the adequate number of threads, which is a source of defect in the final product. In these situations, the information of such a system may be incorrect or misleading.

BRIEF DESCRIPTION

The present invention is constituted by: a sub-system of image acquisition (2) containing the modules of lighting, artificial vision and respective elements of support, fixation, conditioning and adjustment (3); a computerised quality control program composed by a module of morphologic analysis of image for the detection and recognition of overlap of fabric ply, detection and counting of threads or cords in the overlap area, a module of support to the decision process of acceptance/rejection of ply based on the parameters defined by the user and a module for interfacing with production equipment.

BRIEF DESCRIPTION OF THE DRAWINGS

Drawing 1 shows a typical example of an overlap splice of fabric ply used in tyre manufacturing.

Drawing 2 shows the configuration of the system in typical application scenario in the tyre industry.

Figure 1:
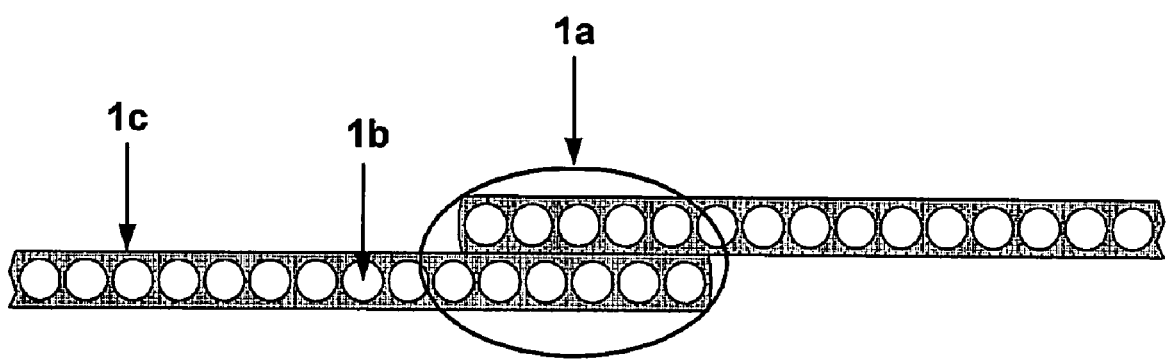
Figure 2:
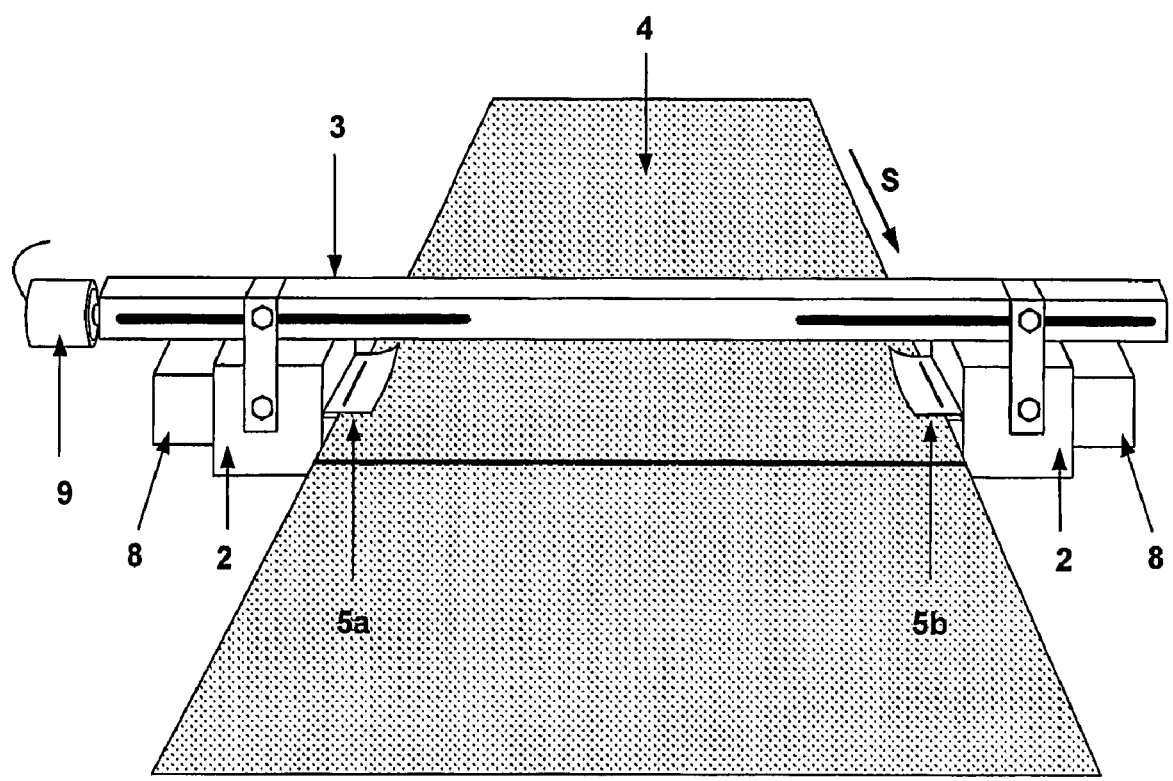
Figure 3:
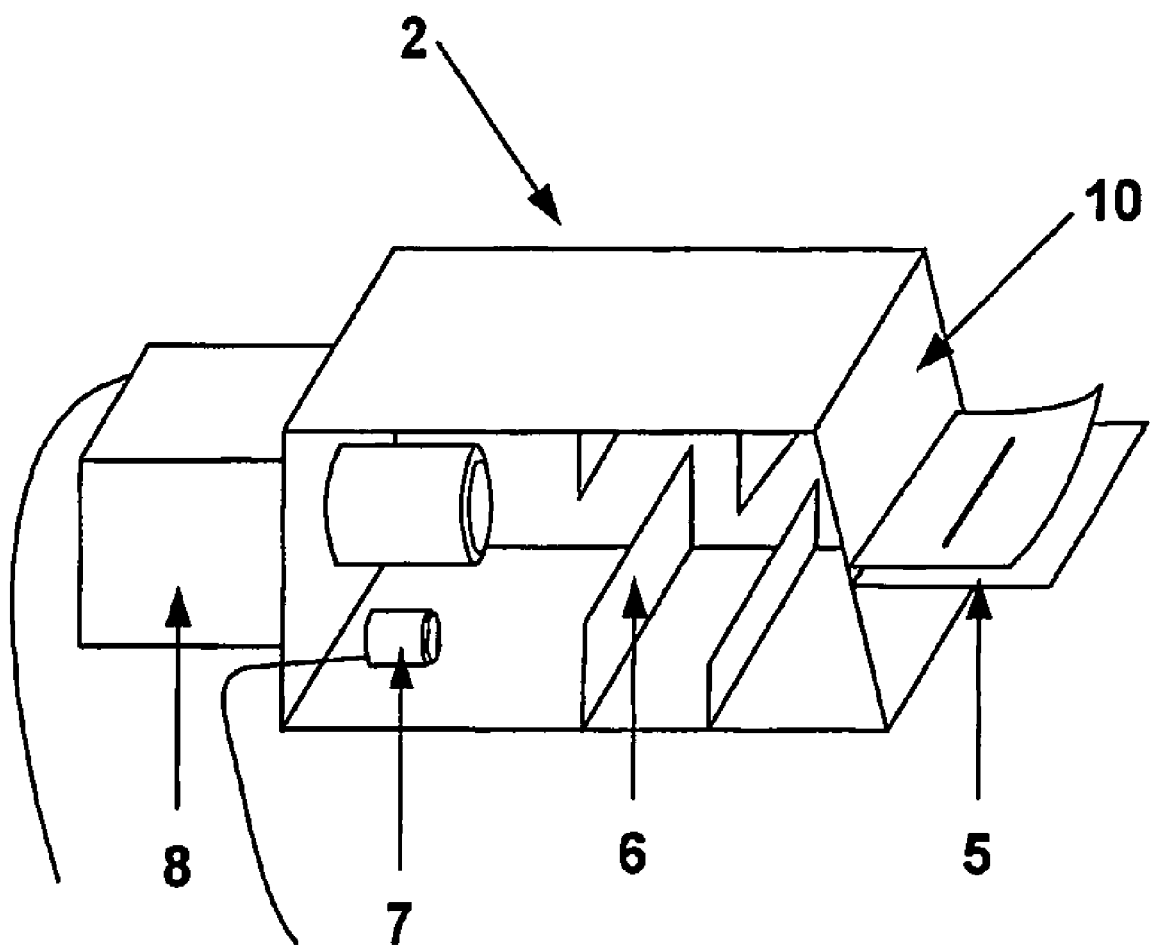

Drawing 3 illustrates the sub-system of image acquisition.

DETAILED DESCRIPTION

The manufacturing of a tyre takes place in different sequential phases: Mixing, Preparation, Building, Curing and Quality Control. In the Preparation phase, the different rubber compounds mixed in the previous phase, Mixing, are used for the production of the components of the pneumatic tyre, amongst which is the textile ply.

This component has the function of guaranteeing the resistance of the tyre through the creation of conditions to contain the air introduced, guaranteeing the support of the intended load. Basically, a roll of textile fabric composed of cords (1b), previously prepared is guided to the calender that will impregnate it with rubber (1c). This ply is later on cut at 90° to the direction of the cord, in a width foreseen for a certain tyre size. The various segments of the ply are spliced overlapping a certain number of cords forming again a sole piece. The ply is rolled up for later usage.

In the calendering of textile fabric, two types of situations that cause imperfections in the overlap splices in the preparation phase of the textile ply, and consequently, cause the non-approval of the tyres in the quality control test, may occur:

Excess rubber on the ends of the fabric—Whenever necessary, in the textile-cutting machine, the excess rubber on the ends of the fabric is removed. If this operation is not done correctly, the overlap is not perfect since in that area there will be, at least in one of the segments, rubber without cords.

Failure of cords—In some situations, when the ply reaches the textile cutter machine, the ply has some cord failures. In this situation there will also not be a perfect overlapping.

If in the textile cutter machine, the overlap splicing process is not correctly adjusted, it may cause splices with an excessive or reduced overlap space. In both cases, the splices will cause imperfections that will imply the non-approval of the tyre in the final quality control tests. A considerable part of the costs of the non-quality tyre production are consequence of these defective overlap splices of textile ply.

The present invention describes a system that enables the identification of the overlap area and the counting of textile cords fabric in that area and the generation of a control signal for the remaining manufacturing equipment. The identification of the overlap area and counting textile cords is done in both extremities of the overlap splice.

The textile ply (4), after being spliced, is placed on a conveyor belt to be rolled up (S) in coils. Upon passing through the ply circulation slots (5a) and (5b) existent in the image acquisition module (2), the acquisition at a rate of 50 frames per second of the two images obtained in both extremities of the overlapping splice is done and are subsequently digitised and processed in real time. The sub-system of image acquisition (2) enables the creation of environmental lighting conditions and protection of the exterior atmosphere that guarantee constant levels of contrast and colour for the gathered images. In practice, these conditions were achieved by adequately positioning the sources of light and equipping the sub-system with conditions to mitigate the internal reflection: internal barriers of light obstruction in the form of partitions (6) duly positioned and diaphragms for incandescence interception, painting with matt dark paint, curtain comprised of bristle bars or bars of any other similar material on the ply circulation slots. This sub-system of image acquisition (2) may be constituted by lighting modules (7) of coherent or incoherent light, in the form of incandescent or fluorescent lamps, LED or laser, or others. With respect to the light characteristics it may be uniform, collimated or structured, with a fixed or sweeping beam, and its wavelength be in the area of visible light spectrum, infra-red or ultra-violet. It may still be stroboscopic, which will enable the synchronisation with the detection process on behalf of the module of artificial vision. Other intrinsic characteristics of light such as its polarisation may also be used. The positioning of sources of light in relation to the ply circulation slot was another issue that was explored and used. This diversity views to mitigate the problems of internal reflection in the casing of the image acquisition module as well as facilitating the identification of the overlap area and of the cords in that area by the computerised quality control program.

The cameras (8) are of CCD type, colour and equipped with an optic system that enables an adequate zoom. The system of support, fixation and adjustment of the image acquisition module (3) was done by a worm screw controlled by an engine (9) that positions the cameras (8) on both extremities of the ply in a symmetrical way.

The acquired images are transferred to a computer, where the quality control program, in the morphologic analysis module, realizes the operations of splice detection and, in its presence, effectuates the counting of the number of cords existent in the overlap.

Upon analysing the profile of the textile ply on the overlap splice area, for this effect, only the splice area where there is overlapping of cords is considered. That is, on a splice where there is excess rubber on the ends of the fabric, both on the superior and inferior part, this overlap space shall not be considered as a splice. This means that a splice must be considered as good or bad, depending on the number of cords only on the overlap area.

According to the specification of the manufacturing process, the stoppage of the splice system is undertaken when the number of cords is beyond the pre-established tolerance limits, through a computer program that supports the decision of acceptance/rejection of the ply, in communication with an interconnection program with the remaining productive equipment, usually done through a programmable logic controller, PLC. The quality control program is sufficiently versatile to enable a great diversity of stoppage criteria, both at individual splices as well as of sequences of splice failures, so as to optimise the quality control process in view of the specific production equipment and of its manufacturing process.

The invention claimed is:

1. An automatic control and monitoring system for splice overlapping tolerance in a textile ply, comprising:
   a. a sub-system of image acquisition containing modules of lighting and artificial vision and respective support, fixing, conditioning and adjustment elements for the modules;
   b. a quality control computer program comprised of the following modules:
   c. morphological analysis of an image for detection and recognition of overlapping of the textile ply, and detection and counting of threads or cords in the overlap area;
   d. support to a decision making process of acceptance/rejection of the ply based on parameters defined by a user; and
   e. interconnection with production equipment.

2. An automatic control and monitoring system for splice overlapping tolerance in the textile ply according to claim 1, wherein the lighting module includes:
   a. a source of light, coherent or incoherent;
   b. a casing to hinder entrance of ambient light; and
   c. a background surface to originate an adequate contrast for the functions of identifying the overlapping region and counting of cords.

3. An automatic control and monitoring system for splice overlapping tolerance in the textile ply according to claim 2, wherein the casing that hinders the entrance of ambient light has a set of partitions duly positioned to diminish the reflection of light lost in walls of the casing.

4. An automatic control and monitoring system for splice overlapping tolerance in the textile ply according to claim 2, wherein the casing that hinders the entrance of ambient light has diaphragms for the interception of incandescence.

5. An automatic control and monitoring system for splice overlapping tolerance in the textile ply according to claim 2, wherein the casing that hinders the entrance of ambient light has, in a ply circulation slot, an external light barrier in the form of curtains or bristle bars.

6. An automatic control and monitoring system for splice overlapping tolerance in the textile ply according to claim 2, wherein the background surface is inclined at an appropriate angle, depending on the visual field of the artificial vision module, to diminish retro-reflection of the background surface onto the artificial vision module.

7. An automatic control and monitoring system for splice overlapping tolerance in the textile ply according to claim 2, wherein the background surface has on an inner surface in the area of a ply circulation slot one or more marks that limit the observation area facilitating its identification by the computerized morphologic analysis program.

8. An automatic control and monitoring system for splice overlapping tolerance in the textile ply according to claim 1, wherein the lighting module has a uniform source of light or radiation.

9. An automatic control and monitoring system for splice overlapping tolerance in the textile ply according to claim 1, wherein the lighting module is constituted by a fixed or a sweeping beam.

10. An automatic control and monitoring system for splice overlapping tolerance in the textile ply according to claim 1, that wherein the lighting module is of collimated light.

11. An automatic control and monitoring system for splice overlapping tolerance in the textile ply according to claim 1, wherein the lighting module is of structured light.

12. An automatic control and monitoring system for splice overlapping tolerance in the textile ply according to claim 1, wherein the lighting module is of visible, infra-red or ultra-violet light.

13. An automatic control and monitoring system for splice overlapping tolerance in the textile ply according to claim 1, wherein the lighting module is of stroboscopic light.

14. An automatic control and monitoring system for splice overlapping tolerance in the textile ply according to claim 1, wherein the lighting module is of polarized light.

15. An automatic control and monitoring system for splice overlapping tolerance in the textile ply according to claim 1, wherein the lighting module is comprised of incandescent lamps, fluorescent lamps, halogen lamps, lasers in solid state, gaseous lasers, laser diodes or light emitting diodes (LED).

16. An automatic control and monitoring system for splice overlapping tolerance in the textile ply according to claim 1, wherein the lighting module has one or more sources of light or radiation positioned frontally to the textile ply or at an angle between −90° and +90°.

17. An automatic control and monitoring system for splice overlapping tolerance in the textile ply according to claim 1, including a device for detection of the thickness of the textile ply, which enables synchronizing the artificial vision module with passage of the overlapping splice region.

18. An automatic control and monitoring system for splice overlapping tolerance in the textile ply according to claim 1, wherein the module of artificial vision has a video camera or cameras of the type CCD.

19. An automatic control and monitoring system for splice overlapping tolerance in the textile ply according to claim 1, wherein the module of artificial vision has a camera or cameras that function in synchrony with a lighting system of stroboscopic light.

20. An automatic control and monitoring system for splice overlapping tolerance in the textile ply according to claim 1, wherein the module of artificial vision has a camera or cameras with polarising filters.

21. An automatic control and monitoring system for splice overlapping tolerance in the textile ply according to claim 1, wherein the sub-system of image acquisition is formed of a mechanical assembly.

22. An automatic control and monitoring system for splice overlapping tolerance in the textile ply according to claim 1, wherein the quality control computer program has a morphological module of image analysis that enables the:
   a. detection and recognition of the overlapping of the textile ply;
   b. detection and counting of cords in the overlap area; and
   c. adjustment of detection in view of the colours and dimension of the ply and of the cords.

23. An automatic control and monitoring system for splice overlapping tolerance in the textile ply according to claim 1, wherein the quality control program has a decision module of acceptance/rejection of the ply.

24. An automatic control and monitoring system for splice overlapping tolerance in the textile ply according to claim 1, wherein the quality control program has an interface module with the production equipment.

25. An automatic control and monitoring system for splice overlapping tolerance in the textile ply according to claim 1, wherein the sub-system of image acquisition further comprises a ply circulation slot.

26. A method for automatically controlling and monitoring overlapping splice tolerance in a textile ply comprising the steps of: providing a textile ply that is for use in a production of a tire and detecting the number of existent cords on the textile ply splices using a system that includes (a) a sub-system of image acquisition containing a lighting module and artificial module and respective support, fixing, conditioning and adjustment elements for the modules; (b) a quality control computer program that includes the following modules: (c) morphological analysis of an image for detection and recognition of overlapping of the textile ply and detection and counting of threads or cords in the overlap area; (d) support to a decision making process of acceptance/rejection of the ply based on parameters defined by a user; and (e) interconnection with product equipment.

* * * * *